(12) United States Patent
Bokrantz et al.

(10) Patent No.: US 10,173,076 B2
(45) Date of Patent: Jan. 8, 2019

(54) SYSTEM AND METHOD FOR DETERMINING A RADIATION TREATMENT PLAN AND A RADIATION THERAPY MACHINE

(71) Applicant: RaySearch Laboratories AB, Stockholm (SE)

(72) Inventors: Rasmus Bokrantz, Stockholm (SE); Björn Hårdemark, Enskededalen (SE); Albin Fredriksson, Stockholm (SE)

(73) Assignee: RAYSEARCH LABORATORIES AB, Stockholm (SE)

(*) Notice: Subject to any disclaimer, the term of this patent is extended or adjusted under 35 U.S.C. 154(b) by 0 days.

(21) Appl. No.: 15/516,091

(22) PCT Filed: Mar. 30, 2016

(86) PCT No.: PCT/EP2016/056848
§ 371 (c)(1),
(2) Date: Mar. 31, 2017

(87) PCT Pub. No.: WO2016/156349
PCT Pub. Date: Oct. 6, 2016

(65) Prior Publication Data
US 2017/0296840 A1    Oct. 19, 2017

(30) Foreign Application Priority Data
Apr. 2, 2015    (EP) .................................... 15162398

(51) Int. Cl.
*A61N 5/10*    (2006.01)
(52) U.S. Cl.
CPC ........... *A61N 5/103* (2013.01); *A61N 5/1045* (2013.01)

(58) Field of Classification Search
CPC .... A61N 5/103; A61N 5/1045; A61N 5/1031; A61N 5/1047; A61N 5/1036;
(Continued)

(56) References Cited

U.S. PATENT DOCUMENTS

| 7,734,010 | B2* | 6/2010 | Otto ..................... A61N 5/1031 378/147 |
| 2009/0252291 | A1* | 10/2009 | Lu ........................ A61N 5/1049 378/65 |

FOREIGN PATENT DOCUMENTS

| WO | WO-2010/025115 A1 | 3/2010 |
| WO | WO-2014/191204 A1 | 12/2014 |

OTHER PUBLICATIONS

Nguyen Dan et al, "Dose domain regularization of MLC leaf patterns for highly complex IMRT plans", Medical Physics, AIP, vol. 42, No. 4, Mar. 25, 2015, p. 1858-p. 1870.

* cited by examiner

*Primary Examiner* — Irakli Kiknadze
(74) *Attorney, Agent, or Firm* — Drinker Biddle & Reath LLP

(57) ABSTRACT

A radiation treatment plan is determined by: [1] receiving a current fluence map defining a radiation dose; [2] receiving a current control-point sequence describing machine settings for a collimator associated with a radiation source; [3] determining an updated fluence map and an updated control-point sequence based on the current fluence map; [4] determining a further updated control-point sequence based on the updated control-point sequence and the updated fluence map; [5] determining a further updated fluence map based on the updated fluence map, the updated control-point sequence and the further updated control-point sequence; [6] checking if a stopping criterion is fulfilled; if so: stopping the process, and producing an output radiation treatment (Continued)

plan based on the further updated control-point sequence; and otherwise: setting the further updated fluence map, or zero, to the current fluence map; setting the further updated control-point sequence to the current control-point sequence; and returning to step [3].

18 Claims, 2 Drawing Sheets

(58) Field of Classification Search
CPC .. A61N 5/1037; A61N 5/1042; A61N 5/1049; A61N 5/1067; A61N 2005/1087; A61N 2005/1089; A61N 2005/1091; A61N 5/1081; A61N 2005/1032; A61N 2005/1074; A61N 5/1071; A61N 5/1039; A61N 2005/1034; A61N 2005/1041; A61N 5/1038; A61N 5/1077; B21D 28/06; B21D 35/00; B65H 2301/5133; G06F 19/321; G06F 19/3481; G16H 40/20
USPC .................................................. 378/4, 62, 65
See application file for complete search history.

SYSTEM AND METHOD FOR DETERMINING A RADIATION TREATMENT PLAN AND A RADIATION THERAPY MACHINE

This application is the National Stage of International Application No. PCT/EP2016/056848, filed Mar. 30, 2016, and claims benefit of European Patent Application No. 15162398.0 filed Apr. 2, 2015.

THE BACKGROUND OF THE INVENTION AND PRIOR ART

The present invention relates generally to radiation therapy and strategies for programming a radiation therapy machine. More particularly the invention relates to a system for determining a radiation treatment plan, a corresponding method and a radiation therapy machine. The invention also relates to a computer program product, a computer readable medium and a radiation therapy method.

Radiation therapy may be employed to treat tumorous tissue. In radiation therapy, a high energy beam of radiation is aimed towards a patient. More precisely, a radiation source produces a beam of radiation that is collimated and directed into a target volume in the patient. The dose and placement of the dose must be accurately controlled to, on one hand, ensure that the tumor receives sufficient radiation; and, on the other hand, that damage to the surrounding healthy tissue is minimized. Before performing the radiation therapy, a radiation treatment plan is determined in a radiation planning session. This allows an accurate and precise dosage of radiation to be delivered to the patient.

WO 2010/025115 describes a method for determining a radiation treatment plan including defining treatment control points, defining dose calculation points, calculating dose in the dose calculation points, and changing a number of the dose calculation points. The proposed method for determining a radiation treatment plan includes modeling a first part of a treatment plan using a fluence map, and modeling a second part of the treatment plan using a first machine parameter. The method for determining a radiation treatment plan includes determining a plurality of dose calculation points, determining a level of complexity of fluence for one or more machine parameters for one of the plurality of dose calculation points based on the determined level of complexity.

A fluence map specifies the irradiance through a surface (e.g. a plane) integrated over time. The fluence map may be represented by a matrix, in which each element indicates the amount of radiation that shall pass through a certain sub-region of the surface. In fluence map optimization, an optimization algorithm determines a fluence map by modifying the matrix elements that represent the fluence map. The goal of the optimization is to improve upon an objective function quantifying, for instance the quality of the dose distribution that would result from the fluence map.

An arbitrary fluence map cannot always be delivered by a treatment machine because of the physical limitations of the machine. Typically, therefore, the fluence map is converted into a control-point sequence describing machine settings (e.g. multi-leaf collimator (MLC) leaf positions, jaw positions, dose rate, delivery time, monitor units, gantry angle) that yield a fluence being as close as possible to the fluence defined by the fluence map. Errors introduced in the conversion can be reduced by direct machine-parameter optimization, in which an optimization algorithm modifies the machine settings of the control point sequence in order to improve upon an objective function quantifying, for example the quality of the dose distribution that would result from the control point sequence.

PROBLEMS ASSOCIATED WITH THE PRIOR ART

Although the known strategy for determining a radiation treatment plan often provides adequate treatment of tumorous tissue there is room for improvements, especially with respect to calculation efficiency for a given accuracy. For example, in the prior-art solution, if the control points resulting from the algorithm prove to be insufficient, additional control points cannot be created by continuing the optimizing process. Namely, after conversion of the fluence map it no longer forms a part of the optimization. Therefore, the optimizing process must be restarted.

SUMMARY OF THE INVENTION

The object of the present invention is therefore to ameliorate the above problem, and thus offer an improved solution for determining a radiation treatment plan for a treatment volume.

According to one aspect of the invention, the object is achieved by a system for determining a radiation treatment plan for a treatment volume associated with at least one target and at least one organ-at-risk. A data processor in the system is configured to calculate, for each of at least one delivery direction, a radiation dose to be delivered to the at least one target. Thus, a control-point sequence is obtained which defines how an amount of radiant energy from a radiation source shall be distributed over a projection area. Specifically, the data processor is configured to calculate the control-point sequence by executing the consecutive steps:

(1) receiving a current fluence map defining a radiation dose to be delivered to the at least one target (e.g. based on a physician's prescription);

(2) receiving a current control-point sequence describing machine settings for a collimator associated with the radiation source, the machine settings defining at least one parameter for an output beam of radiation from the radiation source (Initially, the current control-point sequence may be "empty", or it can be arranged in a default setting);

(3) determining an updated fluence map and an updated control-point sequence based on the current fluence map, the current control-point sequence and an objective function quantifying at least one quality of the radiation dose with respect to a predefined goal;

(4) determining a further updated control-point sequence based on the updated control-point sequence and the updated fluence map, the further updated control-point sequence describing how, with respect to an error-minimizing function, to adjust the machine settings to approximate an amount of radiant energy defined by the updated control-point sequence and the updated fluence map;

(5) determining a further updated fluence map based on the updated fluence map, the updated control-point sequence and the further updated control-point sequence, Preferably, the further updated fluence map is represented by a non-negative residual, which is based on: a first amount of radiant energy defined by a fluence of the updated fluence map, a second amount of radiant energy defined by a fluence of the updated control-point sequence, and a third amount of radiant energy defined by the further updated control-point sequence; and (6) checking if a stopping criterion is fulfilled; if so: stopping the process, and producing an output radiation treatment plan based on the further updated control-point sequence; and otherwise: setting the further updated fluence map (or zero) to the current fluence map, setting the further updated control-point sequence to the current control-point sequence; and returning to step (3).

This system is advantageous because it takes the combined effects of any new control points into account when adding control points to the further updated control-point sequence, which, in the final step, forms the basis for the radiation treatment plan determined by the system. In other words, the proposed system only executes the calculations necessary to achieve a desired treatment accuracy. Moreover, depending on how the stopping criterion is defined, the treatment accuracy can be made very high.

According to one preferred embodiment of this aspect of the invention, the data processor is configured to check if the stopping criterion is fulfilled by: (A1) determining an amount of radiant energy defined by the further updated fluence map, and (A2) checking if the amount of radiant energy defined by the further updated fluence map is less than a threshold amount; or (B) checking if the further updated control-point sequence contains a number of control points, which number exceeds a predefined maximum number. Hence, it is possible to select whether the iterative process shall stop at a particular accuracy level, or when a certain number of control points have been included in the control-point sequence. Naturally, these are very convenient design parameters.

Preferably, the objective function quantifying the at least one quality of the radiation dose with respect to the predefined goal defines a minimal radiation dose in the at least one target and/or a maximal radiation dose in the at least one organ-at-risk. Namely, thereby, a treatment planner may gain straightforward control of the most important parameters of the treatment.

According to another preferred embodiment of this aspect of the invention, the control-point sequence, the updated control-point sequence and the further updated control-point sequence each describes: a set of multi-leaf collimator positions, a set of jaw positions, a gantry angle, a beam energy, a beam type, a dose, a dose rate and/or a point in time relating to monitor units. Thus, any of a radiation therapy treatment plan's key parameters can be optimized.

Further preferably, the control-point sequence, the updated control-point sequence and the further updated control-point sequence include at least two control points which define different multi-leaf collimator positions however provide the same monitor unit; or conversely, include at least two control points which define the same multi-leaf collimator positions however provide different monitor units. Consequently, typical control points for a static multi-leaf collimator (SMLC) may be included in the control-point sequence.

According to another aspect of the invention, the object is achieved by a method of determining a radiation treatment plan for a treatment volume associated with at least one target and at least one organ-at-risk. The method involves calculating, for each of at least one delivery direction, a radiation dose to be delivered to the at least one target, thus obtaining a respective description of how an amount of radiant energy from a radiation source shall be distributed over a projection area. For each of the at least one delivery direction, the method includes the consecutive steps of: (1) receiving a current fluence map defining a radiation dose to be delivered to the at least one target (e.g. based on a physician's prescription); (2) receiving a control-point sequence describing machine settings for a collimator associated with the radiation source, the machine settings defining at least one parameter for an output beam of radiation from the radiation source (Initially, the current control-point sequence may be "empty", or be arranged in a default setting); (3) determining an updated fluence map and an updated control-point sequence based on the current fluence map, the current control-point sequence and an objective function quantifying at least one quality of the radiation dose with respect to a predefined goal; (4) determining a further updated control-point sequence based on the updated control-point sequence and the updated fluence map, the further updated control-point sequence describing how, with respect to an error-minimizing function, to adjust the machine settings to approximate an amount of radiant energy defined by the updated control-point sequence and the updated fluence map; (5) determining a further updated fluence map based on the updated fluence map, the updated control-point sequence and the further updated control-point sequence; (6) checking if a stopping criterion is fulfilled; if so: stopping the process, and producing an output radiation treatment plan based on the further updated control-point sequence; and otherwise: setting the further updated fluence map (or zero) to the current fluence map, setting the further updated control-point sequence to the current control-point sequence; and returning to step (3). The advantages of this method, as well as the preferred embodiments thereof, are apparent from the discussion above with reference to the proposed system.

According to a further aspect of the invention, the object is achieved by a computer program product, which is loadable into the memory of a computer, and includes software for performing the steps of the above proposed method when executed on a computer.

According to another aspect of the invention, the object is achieved by a computer readable medium, having a program recorded thereon, where the program is to make a computer perform the method proposed above when the program is loaded into the computer.

According to yet another aspect of the invention, the object is achieved by a radiation therapy machine configured to receive a radiation therapy treatment plan identified by the above-proposed method, and carry out therapy in accordance with the received radiation therapy treatment plan.

Further advantages, beneficial features and applications of the present invention will be apparent from the following description and the dependent claims.

BRIEF DESCRIPTION OF THE DRAWINGS

The invention is now to be explained more closely by means of preferred embodiments, which are disclosed as examples, and with reference to the attached drawings.

DESCRIPTION OF PREFERRED
EMBODIMENTS OF THE INVENTION

Figure 1:
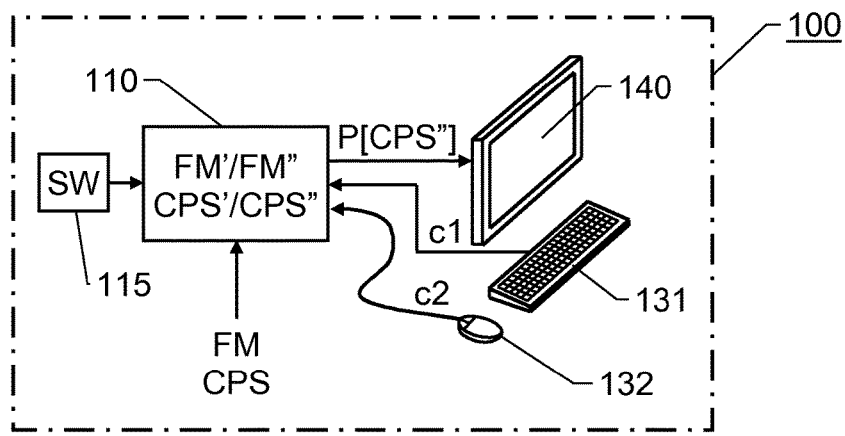
FIG. 1 shows a block diagram over a system according to one embodiment of the invention.

Initially, we refer to FIG. 1, which shows a block diagram over a system 100 according to one embodiment of the invention for determining a radiation therapy treatment plan P[CPS"] for a treatment volume. The treatment volume, in turn, is associated with at least one target (typically represented by tumorous tissue) and at least one organ-at-risk (i.e. healthy tissue, where the amount of radiation shall be kept below certain levels) respectively.

The system includes a data processor 110. Preferably, the system 100 also includes at least one first user interface 131 and 132 configured to receive operator commands c1 and c2 that specify criteria for determining the radiation therapy treatment plan P[CPS"]. Consequently, the first user interface may contain input means, which in FIG. 1, are exemplified by a keyboard 131 (for entering text, numbers and commands) and a mouse 132 (for selecting and confirming selections). However, of course, according to embodiments of the invention, any other form of input means are equally well conceivable, e.g. a touchpad, a touch screen, a voice controlled interface and/or a gaze controlled interface. Further preferably, the system 100 includes at least one second user interface 140 (e.g. a graphical display) configured to present feedback data to the user, such as a description of the determined radiation therapy treatment plan P[CPS"].

The data processor 110 is configured to calculate, for each of at least one delivery direction, a radiation dose to be delivered to the at least one target, thus obtaining a description CPS" of how an amount of radiant energy from a radiation source shall be distributed over a projection area. To accomplish this description for each delivery direction, the data processor 110 is configured to execute the following consecutive steps.

In a first step (1), a current fluence map FM is received (e.g. via the user interface 131/132 or via a data file). The current fluence map FM defines a radiation dose to be delivered to the at least one target. The current fluence map FM is normally based on a physician's prescription defining a dose of radiation deemed necessary to destroy a volume of tumorous tissue in a patient's body.

In a second step (2), a current control-point sequence CPS is received. Typically, at this initial stage, the current control-point sequence CPS has a default value (e.g. being "empty", or designating a default setting), which is stored in the data processor 110. However, analogous to the current fluence map FM, the current control-point sequence CPS may also be entered into the data processor 110 from an external source. In any case, the current control-point sequence CPS describes machine settings for a collimator associated with the radiation source. The machine settings define at least one parameter for an output beam of radiation from the radiation source.

Then, in a third step (3), an updated fluence map FM' and an updated control-point sequence CPS' are determined based on the current fluence map FM, the current control-point sequence CPS and an objective function quantifying at least one quality of the radiation dose with respect to a predefined goal. The objective function quantifying the at least one quality of the radiation dose with respect to the predefined goal may define a minimal radiation dose in the at least one target and/or a maximal radiation dose in the at least one organ-at-risk. Thus, the updated fluence map FM' and the updated control-point sequence CPS' are better than the current fluence map FM and the current control-point sequence CPS with respect to the at least one quality quantified by the objective function.

A subsequent step (4) determines a further updated control-point sequence CPS" based on the updated control-point sequence CPS' and the updated fluence map FM'. The further updated control-point sequence CPS" describes how, with respect to an error-minimizing function, to adjust the machine settings to approximate an amount of radiant energy defined by the updated control-point sequence CPS' and the updated fluence map FM'.

Figure 2:
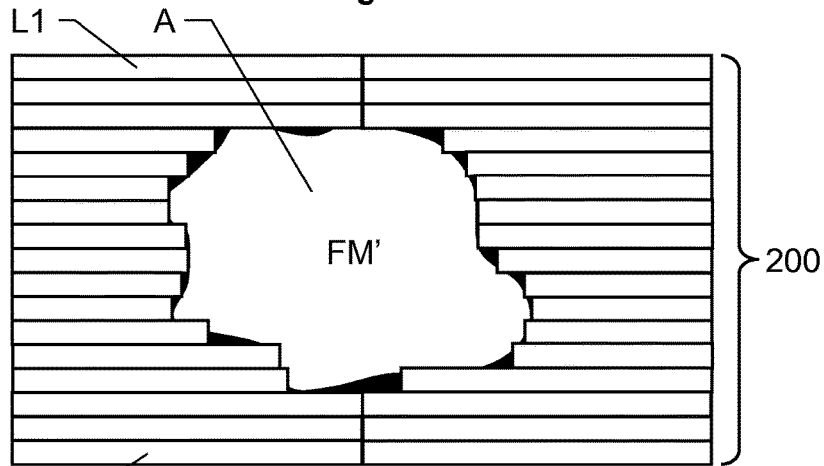
FIG. 2 shows schematic MLC positions defining an aperture for restricting a beam from a radiation source to approximate a fluence map.

FIG. 2 illustrates an example of one aspect of such a further updated control-point sequence CPS". Namely, in FIG. 2, we see a set 200 of leaf pairs L1, . . . , Ln in multi-leaf collimator (MLC) where the leaf pairs L1, . . . , Ln are arranged to accomplish an aperture A for restricting a beam of radiation from a radiation source. Thus, at a given point in time, the aperture A approximates the updated fluence map FM' in a particular direction towards the target volume. In FIG. 2, this two-dimensional aspect of the updated fluence map FM' is represented by the rounded black edges forming the central opening. The aperture A, on the other hand, is symbolized by the gaps between the leaf pairs L1, . . . , Ln. The further updated control-point sequence CPS" defines a sequence of control points, wherein each control point is associated with a particular setting of the leaf pairs L1, . . . , Ln and a point in time at which the leaf pairs L1, . . . , Ln shall be set in these positions. Thus, the further updated control-point sequence CPS" provides a three-dimensional surface, which for each coordinate in a radiance plane designates a particular amount of fluence.

In a step (5), subsequent to step (4), a further updated fluence map FM" is determined based on the updated fluence map FM', the updated control-point sequence CPS' and the further updated control-point sequence CPS".

Then, in a step (6), it is checked if a stopping criterion is fulfilled; and if so, the process is stopped. Thereafter, an output radiation treatment plan P[CPS"] is produced based on the further updated control-point sequence CPS". Here, the output radiation treatment plan P[CPS"] is the radiation treatment plan determined by the system 100.

If, however, the stopping criterion is found not to be fulfilled, the further updated fluence map FM", or zero, is set to the current fluence map FM, and the further updated control-point sequence CPS" is set to the current control-point sequence CPS. Then, the process returns to step (3) for at least one more iteration of steps (3), (4) (5) and (6) to produce a better candidate for the radiation therapy treatment plan P[CPS"] based on an improved further updated control-point sequence CPS".

According to one embodiment of the invention, the stopping criterion checked by the data processor 110 in step (5) relates either to a quality measure or to a complexity measure for the control-point sequence. In practice, therefore, investigating whether or not the stopping criterion is fulfilled, may involve the steps of:

determining an amount of radiant energy defined by the further updated fluence map FM", and checking if the amount of radiant energy defined by the further updated fluence map FM" is less than a threshold amount (i.e. defining a precision measure for the proposed therapy).

Namely, the further updated fluence map FM" represents a non-negative residual that is based on: a first amount of radiant energy defined by a fluence of the updated fluence map FM', a second amount of radiant energy defined by a fluence of the updated control-point sequence CPS' and a third amount of radiant energy defined by the further updated control-point sequence CPS". Thus, a low amount of residual energy means that the control-point sequence provides a good approximation on the desired fluence map.

Alternatively, investigating whether or not the stopping criterion is fulfilled, may involve checking if the further updated control-point sequence CPS" comprises a number of control points exceeding a predefined maximum number. Here, the leaf pairs L1, . . . , Ln (see FIG. 2) represent one example of a potential component of such a complexity measure.

The predefined maximum number may be given by hardware and/or software limitations of the radiation therapy machine which is intended to carry out the planned radiation therapy, or the predefined maximum number can be arbitrarily set by a user.

The data processor 110 preferably contains, or is in communicative connection with a memory unit 115 storing a computer program product SW, which contains software for making the data processor 110 execute the above-described actions when the computer program product SW is run on the data processor 110.

Figure 3:
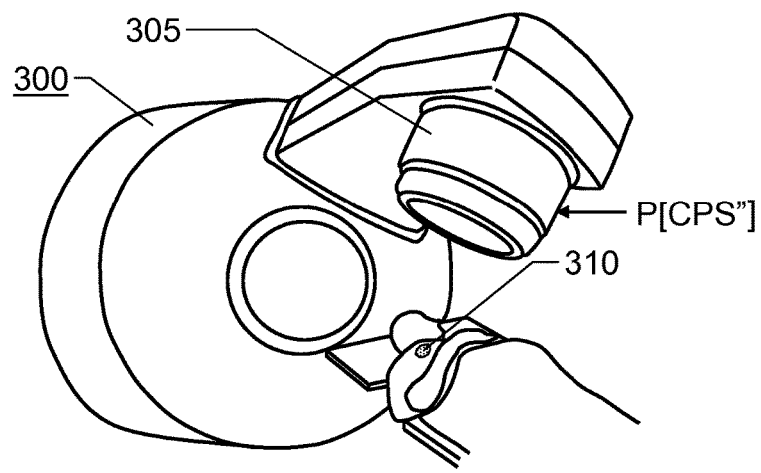
FIG. 3 schematically illustrates a radiation therapy machine according to the invention.

FIG. 3 schematically illustrates a radiation therapy machine 300 according to the invention. The radiation therapy machine 300 is configured to receive the radiation treatment plan P[CPS"] determined by the system 100. The radiation therapy machine 300 is further configured to carry out therapy in respect of the treatment volume 310 in a patient's body by controlling at least one radiation source 305 of the machine 300 in accordance with radiation treatment plan P[CPS"]. Thus, the at least one radiation source 305 may for example be configured to emit radiation towards the treatment volume 310 in the form of photons, electrons, protons, carbon ions or helium ions.

Figure 4:
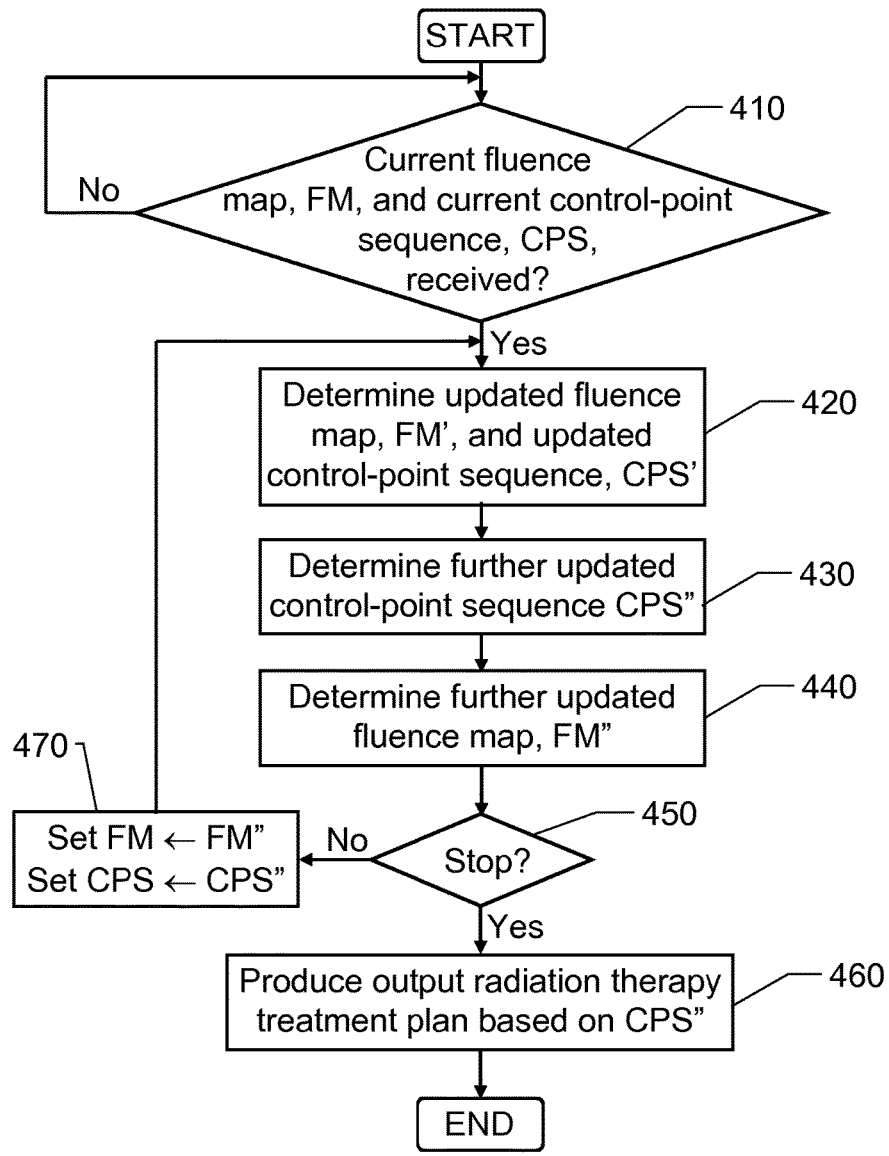
FIG. 4 illustrates, by means of a flow diagram, the general method according to the invention for determining a radiation therapy treatment plan.

In order to sum up, and with reference to the flow diagram in FIG. 4, we will now describe the general method executed in the data processor 110 according to the invention when determining a radiation therapy treatment plan P[CPS"] for a treatment volume 310 associated with at least one target and at least one organ-at-risk.

A first step 410 checks if a current fluence map FM and a current control-point sequence have been received. The current fluence map FM defines a radiation dose to be delivered to the at least one target. As described above, the current fluence map FM may either be entered manually (via user input means) or it can be received automatically (via a data file, e.g. received over a communications link).

The current control-point sequence CPS describes machine settings for a collimator 305 associated with the radiation source. The machine settings, in turn, define at least one parameter for an output beam of radiation from the radiation source. As also mentioned above, in this initial step, current control-point sequence CPS may be trivial (e.g. empty or zero) and for example be given by a default value.

A step 420 then determines an updated fluence map FM' and an updated control-point sequence CPS' based on the current fluence map FM, the current control-point sequence CPS and an objective function quantifying at least one quality of the radiation dose with respect to a predefined goal.

Subsequently, in a step 430, a further updated control-point sequence CPS" is determined based on the updated control-point sequence CPS' and the updated fluence map FM'. The further updated control-point sequence CPS" describes how, with respect to an error-minimizing function, to adjust the machine settings to approximate an amount of radiant energy defined by the updated control-point sequence CPS' and the updated fluence map FM'.

Thereafter, a step 440 determines a further updated fluence map FM" based on the updated fluence map (FM'), the updated control-point sequence CPS' and the further updated control-point sequence CPS".

Then, a step 450 checks if a stopping criterion is fulfilled. If it is found that the stopping criterion is fulfilled, a step 460 follows. Otherwise (i.e. if the stopping criterion is found not to be fulfilled), the procedure continues to a step 470.

In step 460, an output radiation treatment plan P[CPS"] is produced based on the further updated control-point sequence CPS" resulting from step 430, and thereafter the procedure ends.

In step 470, the further updated fluence map FM", or zero, is set to the current fluence map FM; and the further updated control-point sequence CPS" is set to the current control-point sequence CPS. After that, the procedure loops back to step 420 for further refinement of the control-point sequence.

All of the process steps, as well as any sub-sequence of steps, described with reference to FIG. 4 above may be controlled by means of a programmed computer apparatus. Moreover, although the embodiments of the invention described above with reference to the drawings comprise a computer apparatus and processes performed in a computer apparatus, the invention thus also extends to computer programs, particularly computer programs on or in a carrier, adapted for putting the invention into practice. The program may be in the form of source code, object code, a code intermediate to source and object code such as in partially compiled form, or in any other form suitable for use in the implementation of the process according to the invention. The program may either be a part of an operating system, or be a separate application. The carrier may be any entity or device capable of carrying the program. For example, the carrier may comprise a storage medium, such as a Flash memory, a ROM (Read Only Memory), for example a DVD (Digital Video/Versatile Disk), a CD (Compact Disc) or a semiconductor ROM, an EPROM (Erasable Programmable Read-Only Memory), an EEPROM (Electrically Erasable Programmable Read-Only Memory), or a magnetic recording medium, for example a floppy disc or hard disc. Further, the carrier may be a transmissible carrier such as an electrical or optical signal which may be conveyed via electrical or optical cable or by radio or by other means. When the program is embodied in a signal which may be conveyed directly by a cable or other device or means, the carrier may be constituted by such cable or device or means. Alternatively, the carrier may be an integrated circuit in which the program is embedded, the integrated circuit being adapted for performing, or for use in the performance of, the relevant processes.

The term "comprises/comprising" when used in this specification is taken to specify the presence of stated features, integers, steps or components. However, the term does not preclude the presence or addition of one or more additional features, integers, steps or components or groups thereof.

The invention is not restricted to the described embodiments in the figures, but may be varied freely within the scope of the claims.

The invention claimed is:

1. A system for determining a radiation treatment plan for a treatment volume associated with at least one target and at least one organ-at-risk, the system comprising: a data processor configured to calculate, for each of at least one delivery direction, a radiation dose to be delivered to the at least one target, thus obtaining a description of how an amount of radiant energy from a radiation source shall be distributed over a projection area by executing the consecutive steps:
   (1) receiving a current fluence map defining a radiation dose to be delivered to the at least one target;

(2) receiving a current control-point sequence describing machine settings for a collimator associated with the radiation source, the machine settings defining at least one parameter for an output beam of radiation from the radiation source, wherein the data processor is configured to calculate, for each of the at least one delivery direction, the radiation dose to be delivered to the at least one target, by executing the further consecutive steps;

(3) determining an updated fluence map and an updated control-point sequence based on the current fluence map the current control-point sequence, and an objective function quantifying at least one quality of the radiation dose with respect to a predefined goal;

(4) determining a further updated control-point sequence based on the updated control-point sequence and the updated fluence map, the further updated control-point sequence describing how, with respect to an error-minimizing function, to adjust the machine settings to approximate an amount of radiant energy defined by the updated control-point sequence and the updated fluence map, (5) determining a further updated fluence map based on the updated fluence map, the updated control-point sequence, and the further updated control-point sequence;

(6) checking if a stopping criterion is fulfilled; if so: stopping the process, and
producing an output radiation treatment plan based on the further updated control-point sequence; and otherwise:
setting the further updated fluence map, or zero, to the current fluence map,
setting the further updated control-point sequence to the current control-point sequence; and
returning to step (3).

2. The system according to claim 1, wherein the further updated fluence map is represented by a non-negative residual based on:
a first amount of radiant energy defined by a fluence of the updated fluence map,
a second amount of radiant energy defined by a fluence of the updated control-point sequence, and
a third amount of radiant energy defined by the further updated control-point sequence.

3. The system according to claim 1, wherein the data processor is configured to check if the stopping criterion is fulfilled by:
determining an amount of radiant energy defined by the further updated fluence map, and
checking if the amount of radiant energy defined by the further updated fluence map is less than a threshold amount;
or
checking if the further updated control-point sequence comprises a number of control points, which number exceeds a predefined maximum number.

4. The system according to claim 1, wherein the objective function quantifying at least one quality of the radiation dose with respect to the predefined goal defines a minimal radiation dose in the at least one target.

5. The system according to claim 1, wherein the objective function quantifying at least one quality of the radiation dose with respect to the predefined goal defines a maximal radiation dose in the at least one organ-at-risk.

6. The system according to claim 1, wherein the control-point sequence, the updated control-point sequence and the further updated control-point sequence each describes at least one of:
a set of multi-leaf collimator positions, a set of jaw positions, a gantry angle, a beam energy, a beam type, a dose, a dose rate and a point in time relating to monitor units.

7. The system according to claim 1, wherein the control-point sequence, the updated control-point sequence and the further updated control-point sequence include at least two control points defining different multi-leaf collimator positions and providing the same cumulative monitor units.

8. The system according to claim 1, wherein the control-point sequence, the updated control-point sequence and the further updated control-point sequence include at least two control points defining the same multi-leaf collimator positions and providing different cumulative monitor units.

9. A method of determining a radiation treatment plan for a treatment volume associated with at least one target and at least one organ-at-risk, the method comprising:
calculating, for each of at least one delivery direction, a radiation dose to be delivered to the at least one target, thus obtaining a respective description of how an amount of radiant energy from a radiation source shall be distributed over a projection area, wherein, for each of the at least one delivery direction, the method comprises the consecutive steps of:

(1) receiving a current fluence map defining a radiation dose to be delivered to the at least one target;

(2) receiving a current control-point sequence describing machine settings for a collimator associated with the radiation source, the machine settings defining at least one parameter for an output beam of radiation from the radiation source;

(3) determining an updated fluence map and an updated control-point sequence based on the current fluence map, the current control-point sequence and an objective function quantifying at least one quality of the radiation dose with respect to a predefined goal;

(4) determining a further updated control-point sequence based on the updated control-point sequence and the updated fluence map, the further updated control-point sequence describing how, with respect to an error-minimizing function, to adjust the machine settings to approximate an amount of radiant energy defined by the updated control-point sequence and the updated fluence map, (5) determining a further updated fluence map based on the updated fluence map, the updated control-point sequence and the further updated control-point sequence, (6) checking if a stopping criterion is fulfilled; if so: stopping the process, and
producing an output radiation treatment plan based on the further updated control-point sequence;
and otherwise:
setting the further updated fluence map, or zero, to the current fluence map,
setting the further updated control-point sequence to the current control-point sequence; and
returning to step (3).

10. The method according to claim 9, wherein the further updated fluence map is represented by a non-negative residual between a first amount of radiant energy defined by a fluence of the further updated control-point sequence and a second amount of radiant energy defined by the updated fluence map.

11. The method according to claim 9, wherein checking if the stop criterion is fulfilled involves:
    determining an amount of radiant energy defined by the further updated fluence map, and
    checking if the amount of radiant energy defined by the further updated fluence map is less than a threshold amount;
    or
    checking if the further updated control-point sequence comprises a number of control points, which number is equal to a predefined maximum number.

12. The method according to claim 9, wherein the objective function quantifying at least one quality of the radiation dose with respect to the predefined goal defines a minimal radiation dose in the at least one target.

13. The method according to claim 9, wherein the objective function quantifying at least one quality of the radiation dose with respect to the predefined goal defines a maximal radiation dose in the at least one organ-at-risk.

14. The method according to claim 9, wherein the control-point sequence, the updated control-point sequence and the further updated control-point sequence each describes at least one of:
    a set of multi-leaf collimator positions, a set of jaw positions, a gantry angle, a beam energy, a beam type, a dose, a dose rate, and a point in time relating to monitor units.

15. The method according to claim 9, wherein the control-point sequence, the updated control-point sequence and the further updated control-point sequence include at least two control points defining different multi-leaf collimator positions and providing the same cumulative monitor units.

16. The method according to claim 9, wherein the control-point sequence, the updated control-point sequence and the further updated control-point sequence include at least two control points defining the same multi-leaf collimator positions and providing different cumulative monitor units.

17. A computer program product loadable into a non-transitory memory of at least one computer, comprising software configured to cause the at least one computer to perform the steps of the method according to claim 9 when executed on the at least one computer.

18. A non-transitory computer readable medium having a program recorded thereon, where the program is to make at least one computer perform the steps of the method according to claim 9 when executed on the at least one computer.

* * * * *